United States Patent [19]
Hughes et al.

[11] Patent Number: 6,129,823
[45] Date of Patent: Oct. 10, 2000

[54] LOW VOLUME ELECTROCHEMICAL SENSOR

[75] Inventors: Graham John Hughes, Headington; Simon William Bayliff, Abindgon; Geoffrey Roger Chambers, Northwood, all of United Kingdom

[73] Assignee: Abbott Laboratories, Abbott Park, Ill.

[21] Appl. No.: 08/926,326

[22] Filed: Sep. 5, 1997

[51] Int. Cl.[7] .................................................. G01N 27/26
[52] U.S. Cl. ........................ 204/409; 204/403; 204/415
[58] Field of Search ................................. 204/409, 403, 204/416, 415; 435/817

[56] References Cited

U.S. PATENT DOCUMENTS 4,672,970  6/1987  Uchida et al. ............................ 600/360
5,628,890  5/1997  Carter et al. .............................. 204/403

FOREIGN PATENT DOCUMENTS 0593096  4/1994  European Pat. Off. .

*Primary Examiner*—Jill Warden
*Assistant Examiner*—Alex Noguerola
*Attorney, Agent, or Firm*—David L. Weinstein

[57] ABSTRACT

An electrochemical sensor electrode strip that measures analyte concentration in an aqueous sample as small as 2.5 to 2.0 μL is described. Reduction in the minimum sample size is achieved by means of a dielectric coating impregnated into peripheral regions of one or more hydrophilic mesh layers, thereby reducing sample dead volume. The mesh layers are located between an electrode support and a cover layer, which cover layer includes an aperture located upstream from an electrode arrangement.

22 Claims, 3 Drawing Sheets

LOW VOLUME ELECTROCHEMICAL SENSOR

FIELD OF THE INVENTION

The invention relates to electrochemical sensors, biomedical testing, and blood analysis.

BACKGROUND OF THE INVENTION

Electrochemical assays for determining the concentration of enzymes or their substrates in complex liquid mixtures have been developed. For example, electrochemical sensor strips have been developed for the detection of blood glucose levels. Electrochemical sensor strips generally include an electrochemical cell in which there is a working electrode and a reference electrodes. The potential of the working electrode typically is kept at a constant value relative to that of the reference electrode.

Electrochemical sensor strips are also used in the chemical industry and food industry, to analyze complex mixtures. Electrochemical sensors are useful in biomedical research, where they can function as invasive probes, and for external testing (i.e., testing of blood obtained by a needle and syringe, or a lance).

Typical electrochemical sensors for blood analysis measure the amount of analyte in a blood sample by using a working electrode coated with a layer containing an enzyme and a redox mediator and a reference electrode. When the electrodes contact a liquid sample containing a species for which the enzyme is catalytically active, the redox mediator transfers electrons in the catalyzed reaction. When a voltage is applied across the electrodes, a response current results from the reduction or oxidation of the redox mediator at the electrodes. The response current is proportional to the concentration of the substrate. Some sensors include a dummy electrode coated with a layer containing the redox mediator and lacking the enzyme that improves the accuracy and precision of the measurements.

Thin layer electrochemical sensors that have electrodes confined in a covered region of the sensor generally have a venting system for releasing air from the confined electrode region upon displacement by the sample. In a two-mesh electrode construction, the sample wicks along the primary layer and the displaced air is vented from the second mesh layer. See, e.g., U.S. Pat. No. 5,628,890.

Reducing the total sample volume necessary to produce a precise and accurate analyte concentration reading by an electrochemical sensor would enhance user convenience. Reducing sample volume is particularly desirable in a blood analysis, because pain, messiness, and time required to stop bleeding generally increase as blood sample size increases.

Although sample size reduction is desirable, various constraints severely limit the ways in which this can be accomplished. Constraints include the following. Sample volume must be sufficient to cover the entire electrode area. Reducing electrode area changes the electrode response current, thereby rendering an electrode strip incompatible with a given meter. Where the sample is not applied directly to an electrochemical cell, the total volume required includes the volume necessary to cover a sample loading zone, and a path to the electrodes, as well as the electrode area. The sample loading zone must be easily visible, even to diabetics with impaired vision.

SUMMARY OF THE INVENTION

The invention features an electrode strip for use in an electrochemical sensor for measuring an analyte in an aqueous sample. For various reasons, it can be desirable to apply a sample at one location on an electrode strip and transport all or part of the sample to an electrode area at a different location. This arrangement requires a portion of the sample to fill up a travel path from the sample loading area to the electrode area, i.e., a sample dead volume. The invention features an electrode strip with a reduced sample dead volume. This permits analyte measurement on a sample as small as 2.0 to 2.5 $\mu$L.

The electrode strip includes an electrode support and an electrode arrangement on the support. The electrode arrangement includes a working electrode and a reference electrode. The working electrode has an upstream end and a downstream end, and the reference electrode is adjacent to the downstream end of the working electrode. Optionally, the electrode arrangement also includes a dummy electrode.

One or more hydrophilic mesh layers overlay the sample loading area and the electrode arrangement, with the sample loading area being adjacent to the upstream end of the working electrode. A cover layer defines an upper boundary of a cell volume enclosing the electrode arrangement. The cover layer has an aperture located above the sample loading area, with no portion of the aperture located above the electrode arrangement. A dielectric coating impregnates the peripheral regions of the mesh layers, thereby forming an occluded region of the mesh layers. The occluded region overlays a portion of the sample loading area and also defines the side boundaries of the cell volume. The occluded region overlays no portion of the electrode arrangement. The mesh layers draw the sample from the sample loading area into the area immediately above the electrodes, via a sample flow channel, whereby the sample contacts the electrodes.

The electrode strip includes one or more hydrophilic mesh layers. Preferably, the mesh layers have a total thickness between 40 and 200 $\mu$m. The mesh layers can be made of an inherently hydrophilic mesh material, or a mesh material coated with a surfactant. Preferably, the mesh material is woven nylon, coated with a surfactant such as FC 170C FLUORAD™. Preferably the mesh layers include a woven mesh material having an open area of about 40 to about 45%, a mesh count of about 95 to about 115 strands per centimeter, a strand diameter of about 20 to about 40 $\mu$m, and a thickness of from about 40 to about 60 $\mu$m.

Preferably, the cover layer is substantially impermeable to aqueous liquids. A suitable cover layer is a polyester membrane.

Typically, the electrode strip is between 4.5 and 6.5 mm wide. Typically, the aperture has a width between 2.5 and 3.5 mm and a length between 2.5 and 3.5 mm. For an electrode strip and aperture of these dimensions, the sample path length (i.e., distance from the upstream end of the non-occluded area of the mesh to the downstream end of the non-occluded area) preferably is between 6 mm and 10 mm. More preferably, the sample path length is between 7 mm and 9 mm.

Preferably, the dielectric coating is a hydrophobic material such as POLYPLAST™ or SERICARD™. The dielectric coating forms an occluded region in the mesh layers. The occluded region forms a sample flow channel in the sample loading area. Preferably, the width of the sample flow channel is between 4 mm and 0.5 mm. The width can be uniform or nonuniform. Preferably, the sample flow channel widens in the direction of said electrode arrangement, e.g., the sample flow channel is V-shaped. Preferably, the sample flow channel represents between 10 and 50% of the mesh layer area within the aperture.

Another feature of the invention is a means of identifying the target area of the electrode by providing a contrast color within the sample loading area. The insulating layer can be colored to contrast with the cover layer, the electrode support, or both. This provides a contrast color at the target area where the sample is applied to the strip that can assist the user in correctly applying the sample to the strip.

Other features and advantages of the invention will be apparent from the description of the preferred embodiment thereof, and from the claims.

BRIEF DESCRIPTION OF THE DRAWINGS

FIGS. 4A–4F illustrate examples of sample flow channel patterns or geometries according to the invention.

In FIG. 5A, the cover layer is present. In FIG. 5B, the cover layer has been removed.

DESCRIPTION OF THE PREFERRED EMBODIMENTS

Sample volume must be great enough to cover the entire electrode area, including the working electrode, reference electrode, and dummy electrode, if present. Incomplete coverage of the entire electrode area can cause erroneous measurements.

Working electrode area and dummy electrode area must be compatible with electrical current requirements of the meter system with which the electrode strip is used. The current response generated by the electrodes and measured by the meter is directly proportional to the area of the working and dummy electrodes. Changes in response current caused by changes in electrode area will make the electrode incompatible with calibration parameters in a previously compatible meter system.

Thin layer sensors having electrodes in a covered area of an electrode strip require a sample loading zone from which the sample travels to the electrode area. This imposes a volume requirement greater than the volume required to cover the electrode area alone. The total volume requirement thus equals the volume required to cover the electrode area plus the sample loading area plus the sample flow channel area between them.

Proper sample application is essential for accurate and reliable operation of an electrochemical sensor system. Therefore, the sample loading area must have a size and color that make it easily visible to the user, including diabetic users, who often have impaired vision. The size of the application zone significantly affects sample dead volume.

The thickness of the sample layer between the electrode surface and the electrode strip cover layer is determined by the thickness of mesh layers used in strip construction. The electrochemical assay reaction can occur in a thinner section of the sample layer than that required to transport the sample to the electrode area by wicking through the mesh. Therefore, a further dead volume constraint is associated with the mesh layers.

By locating the reference electrode downstream from the working electrode, a circuit is not established until the working electrode has been completely covered by the sample and the sample has reached the reference electrode. Consequently, a response is not detected if the sample inadequately covers the working electrode. The mesh layer and the dielectric coating can contribute to the movement of the sample towards the working electrode and reference electrode in a uniform manner. The electrode arrangement can prevent the sample from reaching the reference electrode until the working electrode is substantially or completely covered.

Figure 1:
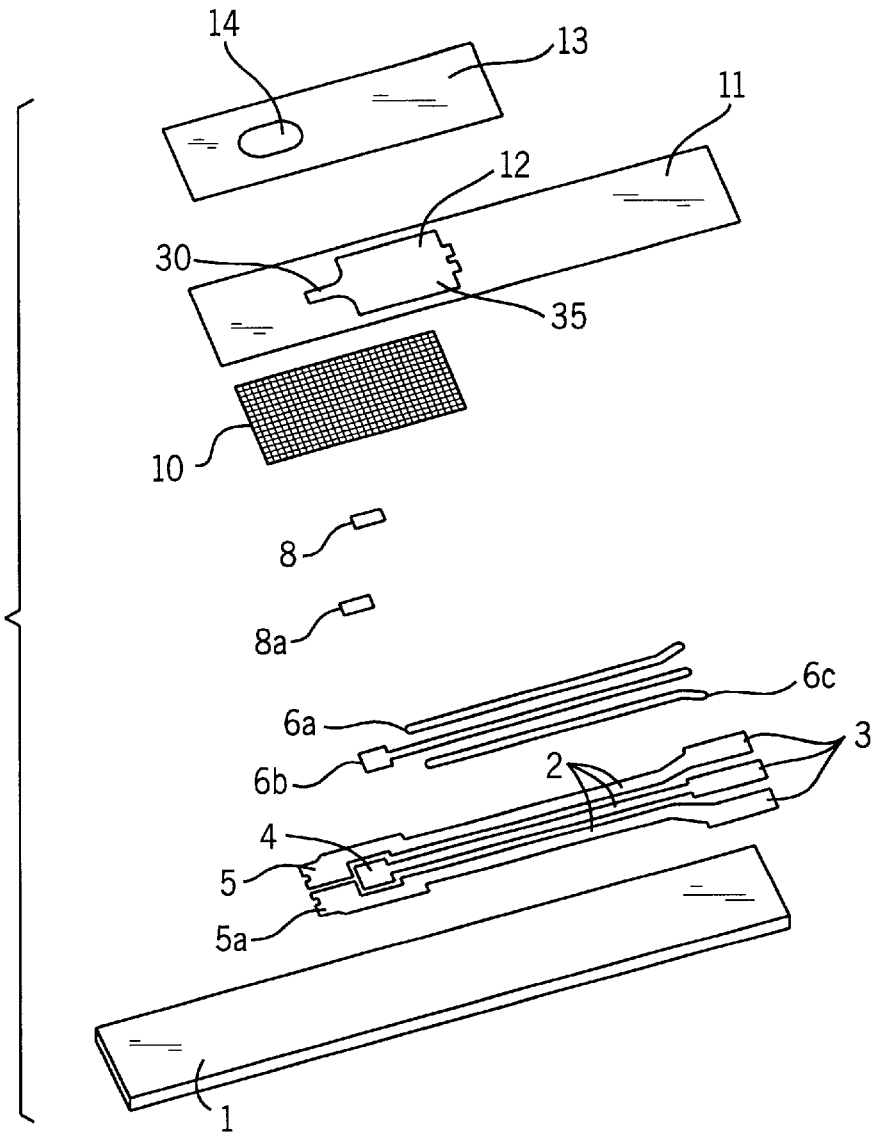
FIG. 1 is an exploded view of an electrode strip according to one embodiment of the invention.
Figure 2:
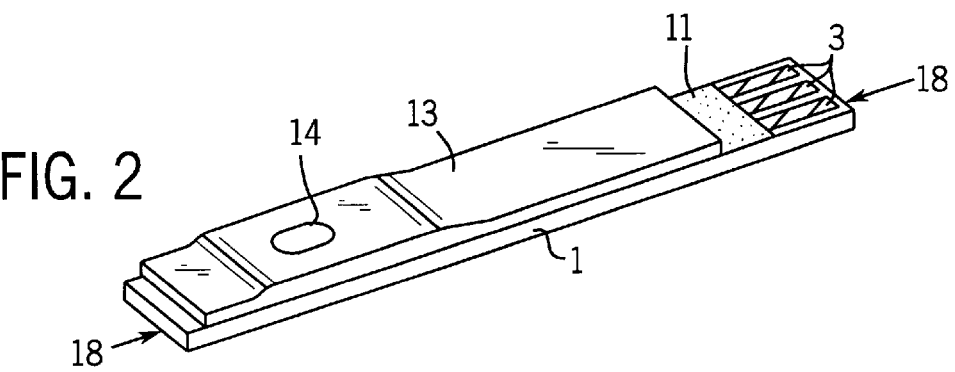
FIG. 2 is a perspective view of the assembled strip of FIG. 1.

An embodiment of the electrode strip is illustrated in FIGS. 1 and 2. Referring to FIGS. 1 and 2, the electrode support 1 is an elongated strip of plastic such as PVC, polycarbonate, or polyester. It supports three printed 1.tracks of electrically conducting carbon ink 2. The printed tracks define the positions of the reference electrode 4, the working electrode 5, the dummy electrode 5a, and the electrical contacts 3. The contacts 3 are for insertion into a compatible meter. The elongated portions of the conductive tracks are each overlaid with silver/silver chloride particle tracks 6a, 6b, 6c. Elements 6b and 4 together form the reference electrode.

The working electrode working area 8 is formed from an ink that includes an enzyme, a mediator, and a filler. The working area ink forms a slurry with the sample. The dummy electrode working area 8a is formed from ink that includes a mixture of a mediator and a filler, without enzyme. The respective inks are applied to the positions 5 and 5a of carbon tracks 2 as discrete areas of fixed length. Alternatively, electrode layer 8 can contain a substrate catalytically reactive with an enzyme to be assayed. The conductive material in a preferred embodiment includes particulate carbon having the redox mediator adsorbed thereon.

An electrode printing ink includes a filler, e.g., carbon, and adsorbed redox mediator. Ink for the working electrode also includes an enzyme or a substrate. When the analyte to be measured is blood glucose, the enzyme is preferably glucose oxidase, and the redox mediator is preferably a ferrocene derivative.

The ink can be screen printed. The ink can include an enzyme stabilizer, a film-forming polymer, a filler (e.g., carbon), a redox mediator (e.g., ferrocene or a ferrocene derivative), a buffer, and an enzyme or a substrate. The ink printed on a dummy electrode lacks the enzyme or the substrate.

A surfactant coated mesh layer 10 overlays the electrode arrangement. The mesh layer protects the printed components from physical damage, and facilitates wetting of the electrodes by the aqueous sample. Preferably, the mesh layer extends over the entire sample path, between and including, the sample application area and the electrode arrangement. The mesh can be made of finely woven nylon. Alternatively, any woven or non-woven material can be used. Preferably, the fabric is not more than 70 $\mu$m in thickness. Preferably the mesh has a percent open area of about 40 to about 45%, a mesh count of about 95 to about 115 per cm, a fiber diameter of about 20 to about 40 $\mu$m, and a thickness of from about 40 to about 60 $\mu$m. A particularly suitable mesh is NY64 HC mesh, available from Sefar (formerly ZBF), CH-8803, Ruschlikon, Switzerland.

If the mesh material is hydrophobic (e.g., nylon or polyester), it is coated with a surfactant. If a hydrophilic mesh is used, the surfactant coating can be omitted. Hydrophilicity of the mesh allows the sample to wick along the mesh layer to the electrodes. The wicking properties of the mesh can be controlled by changing the type or amount of surfactant on the mesh material. Various surfactants are suitable for coating the mesh material. A preferred surfactant is FC 170C FLUORAD™ fluorochemical surfactant (3M, St. Paul, Minn.). FLUORAD™ is a solution of a fluoroaliphatic oxyethylene adduct, lower polyethylene glycols, 1,4-dioxane, and water.

The preferred surfactant loading will vary depending on the type of mesh and surfactant used and the sample to be analyzed. It can be determined empirically by observing flow of the sample through the mesh with different levels of surfactant. If two mesh layers are used, the second (upper) mesh layer preferably is hydrophilic, but not more hydrophilic than the first (lower) mesh layer. Accordingly, the first mesh layer can have a greater load of surfactant than the second mesh layer. With regard to the first mesh layer, suitable surfactant loading for most applications is about 15–20 μg/mg of mesh (i.e., about 1.0 percent w/v). With regard to the second mesh layer, suitable surfactant loading for most applications is about 1–10 μg/mg of mesh.

The mesh layer 10 is held in place by a dielectric coating 11, which impregnates the periphery of the mesh layer. The dielectric coating can be applied by screen printing. The dielectric coating 11 covers no portion of the electrode arrangement. Preferably, the dielectric coating is hydrophobic, so that it efficiently confines the sample. A preferred hydrophobic dielectric coating is POLYPLAST™ (Sericol Ltd., Broadstairs, Kent, UK). A more preferred hydrophobic dielectric coating is SERICARD™ (Sericol).

The uppermost layer on the electrode strip is a cover membrane 13, which can be substantially impermeable. A preferred cover layer is a flexible polyester tape.

The cover layer defines an upper boundary of the electrochemical cell volume, and thus, the cover layer determines the maximum depth of the aqueous sample. The cover layer fixes the upper boundary of the cell volume at a predetermined height, which depends on the thickness of the mesh layers. The cell height, and thus maximum sample depth, is selected to ensure a suitably high solution resistance.

The cover layer has an aperture 14 for sample access to the underlying mesh layers. The aperture 14 is located over the sample loading area, which is adjacent to the upstream end of the working electrode. The aperture can be of any suitable size large enough to allow sufficient volume of sample to pass through to the mesh layer. It should not be so large as to expose any portion of the electrode arrangement. The aperture can be formed in the cover layer by any suitable method, e.g., die punching.

In FIG. 1, the dielectric coating 11 forms a V-shaped sample flow channel 30. The dielectric coating 11 surrounds the sample path (sample flow channel plus electrode area) 12, and this geometry reduces the total volume of sample that needs to be applied to the strip. The V-shape of flow channel 30 helps direct the sample toward the electrodes. The dielectric coating 11 can have a color that contrasts with the color of cover layer 13, the color of electrode support 1, or both. The color contrast enhances visibility of the aperture 14, thereby facilitating proper application of a sample to the electrode strip.

Cover layer 13 is peripherally affixed to the strip by means of a suitable adhesive. The cover layer 13 is not affixed in the area of the electrode arrangement or the sample flow channel. Preferably, the cover layer 13 is affixed by means of a hot melt adhesive. The hot melt adhesive typically has a coating weight between 10 and 50 g/m$^2$, preferably from 20 to 30 g/m$^2$. Pressure sensitive adhesives or other suitable adhesives can also be used. When a heat sensitive dielectric coating is used, e.g., SERICARD™, heat welding of the cover layer should be carried out in a manner that does not damage the dielectric coating.

An adhesive is applied so that the dielectric coating 11 is partially sealed to the cover layer 13, mesh layer 10, and electrode support 1. The layers are adhered to the electrode support by applying pressure and heat in discrete areas on both sides and each end of the electrode strip. Heat and pressure are not applied to the central portion of the strip, which contains the electrode arrangement. Preferably, a portion of the cover layer is not sealed to the dielectric coating. When a sample is applied to the target area of the electrode at aperture 14, the sample passes beneath cover layer 13 through the surfactant coated mesh layer 10, toward the electrodes 4, 5, and 5a.

Optionally, the upper surface of the cover layer can be coated with a layer of silicone or other hydrophobic coating. This helps to drive the applied sample onto the hydrophlic mesh layer at the sample loading area, thus facilitating the application of small volumes.

In use, a sensor strip of the invention is connected, via electrode contacts 3, to a measuring device (not shown). A sample is applied to the sample loading area via aperture 14. The sample moves along the sample flow channel 12. Sample movement is sufficiently impeded by mesh layer 10 so that the sample advantageously forms a uniform front. Air is displaced thorough the upper portion of mesh layer 10 to and through aperture 14. The sample entirely covers working electrode 5 before reaching reference electrode 4. Arrival of the sample front at the reference electrode completes the circuit and causes a response to be detected by the measuring device.

In some embodiments of the invention, a second mesh layer is used over the first mesh. The second mesh layer can further control the flow of the sample as it travels from the application point toward the electrodes. The second mesh layer can be coated with a surfactant. Preferably, the second mesh layer is hydrophilic, but not more hydrophilic that the first mesh layer. If necessary, the first mesh layer can have a greater load of surfactant than the second mesh layer.

Preferably, the second mesh layer is woven, so that A it presents a regular repeating pattern of mesh fibers perpendicular to, and parallel with, the long axis of the electrode strip. Preferably, the second mesh layer is substantially thicker than the first mesh, with larger diameter mesh fibers and larger openings. The second mesh layer can have a thickness of about 100 to 1000 μm, with a thickness of 100 to 150 μm being preferred. Preferably, the second mesh has a percent open area of about 50 to 55%, a mesh count of about 45 to about 55 strands per cm, and a strand diameter of about 55 to about 65 μm. A suitable mesh for use as a second mesh layer is NY151 HC mesh (Sefar, Ruschlikon, Switzerland).

Figure 4A:
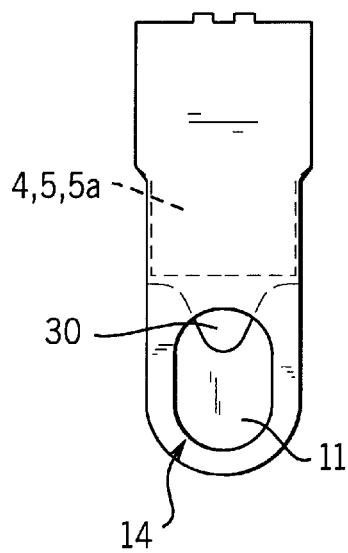
FIGS. 4A–4F are top views of apertures and sample loading areas of low volume electrode strips.
Figure 4B:
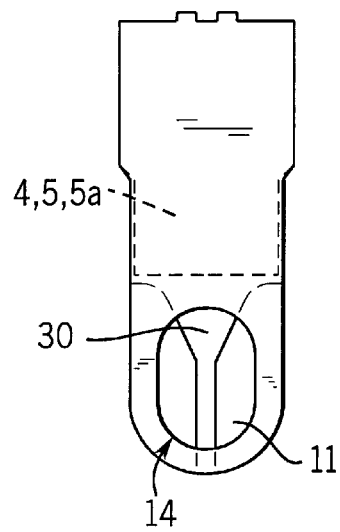
Figure 4C:
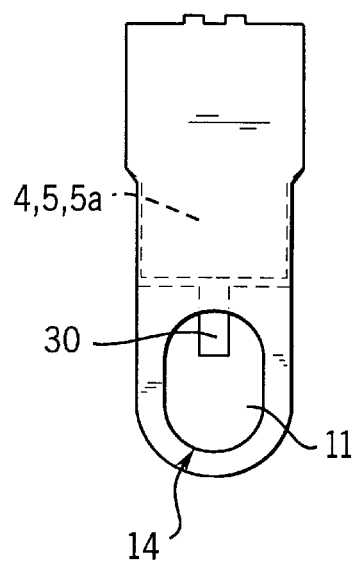
Figure 4D:
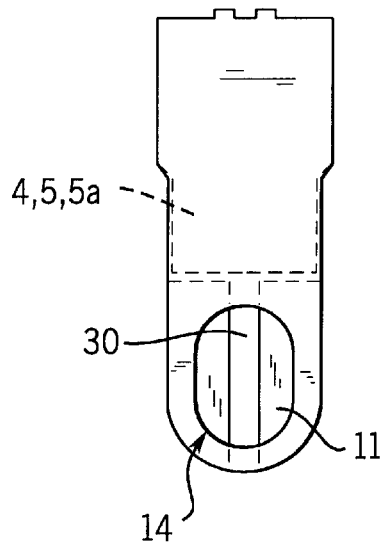
Figure 4E:
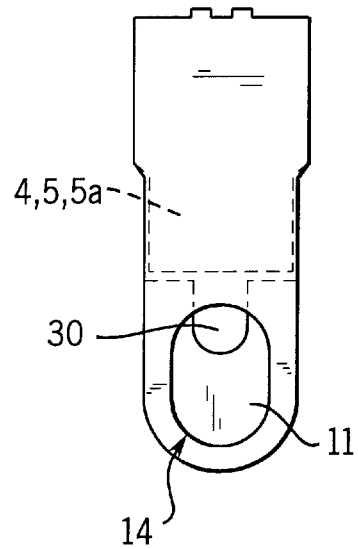
Figure 4F:
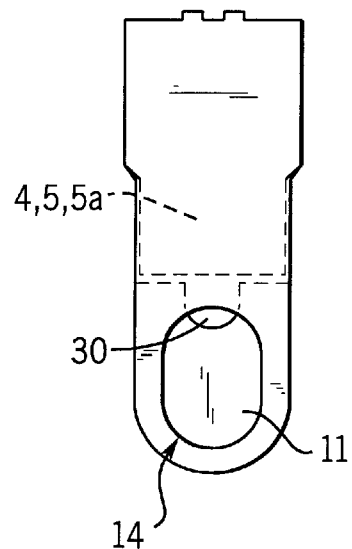

Referring to FIGS. 4A–4F, the pattern or geometry of the sample flow channel 30, can vary. The sample flow channel 30 is formed by impregnation of a hydrophobic dielectric coating 11 into all mesh layers present. The aperture 14 allows access of the sample to the sample flow channel 30, which directs the sample to the electrodes 4, 5, 5a. In the embodiments of the invention shown in FIGS. 4A–4F, the aperture 14 is 2.35 mm wide by 3.35 mm long, and the total area beneath the aperture 14 is 6.7 mm². In FIGS. 4A–4F, the non-occluded areas within the apertures are as follows: FIG. 4A, 1.28 mm²; FIG. 4B, 2.73 mm²; FIG. 4C, 0.76 mm²; FIG. 4D, 2.05 mm²; FIG. 4E, 1.61 mm²; and FIG. 4F, 0.67 mm².

Figure 5A:
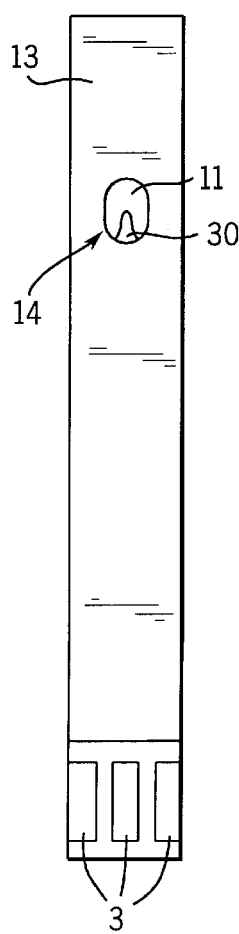
FIGS. 5A and 5B are top views of a preferred embodiment of the invention.
Figure 5B:
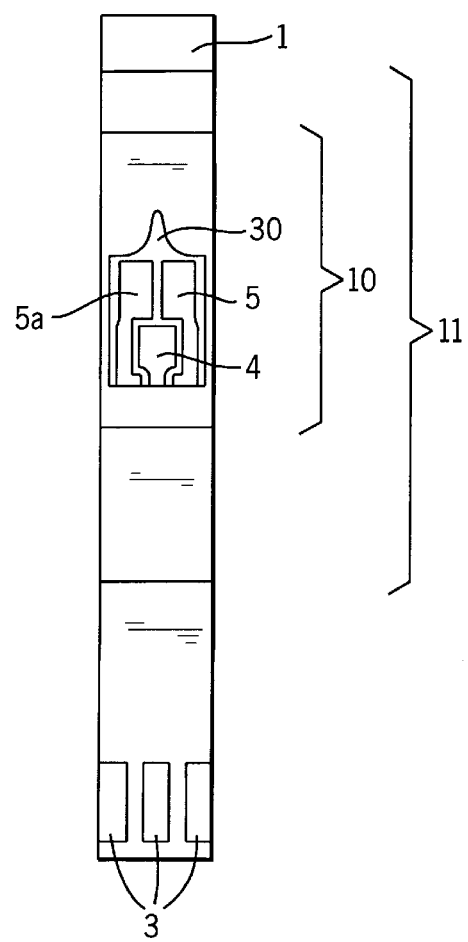

FIGS. 5A and 5B depict a preferred embodiment of the invention. In FIG. 5A, an oval-shaped aperture 14 in the cover layer 13 exposes a sample flow channel 30 and a portion of the dielectric coating 11 that forms the sample flow channel 30. In FIG. 5B, the cover layer 13 has been removed to show the mesh layer 10 and electrodes 4, 5, 5a.

The following examples are intended to be illustrative and not limiting of the invention.

EXAMPLES

Low volume electrode strips were constructed with a single mesh layer (NY151, Open area 37%, mesh count 41/cm, thickness 150 μm) held down with a single layer of dielectric coating (Sericard™). Another set of electrode strips was constructed with two mesh layers. The dielectric coating formed a sample flow channel essentially as shown in FIG. 1.

Venous blood samples were obtained and divided into aliquots. A known amount of glucose was added to each aliquot to make a series of whole blood samples with a range of glucose concentrations between 90 mg/dl (5 mM) and 820 mg/dl (45 mM). A small volume (3–5 μl) from each aliquot was applied to the sample loading areas of the above-described strips, and to control strips, for comparison. The control strips had two mesh layers and did not have a sample flow channel formed by the dielectric coating occluding part of the mesh layer area. Responses of the strips to the glucose in the samples were measured using a compatible meter system. The measured steady state responses for both the sample and control electrodes were plotted against glucose level. The results are summarized in Table 1. The low volume electrode strips gave a linear glucose response essentially the same as that of the prior art electrode strips. Neither the reduction in sample thickness by the use of a single mesh layer, nor the use of a sample flow channel materially affected the response.

TABLE 1

| Glucose mg/dl | Single Mesh Response (μC) | Double Mesh Response (μC) |
|---|---|---|
| 0 | | |
| 91 | 9.0 | 7.8 |
| 172 | 16.4 | 15.9 |
| 272 | 24.8 | 25.8 |
| 351 | 31.7 | 31.0 |
| 441 | 36.8 | 40.8 |
| 533 | 44.1 | 48.4 |
| 641 | 5D.9 | 52.9 |
| 715 | 52.8 | 57.0 |
| 820 | 57.1 | 62.9 |

Figure 3:
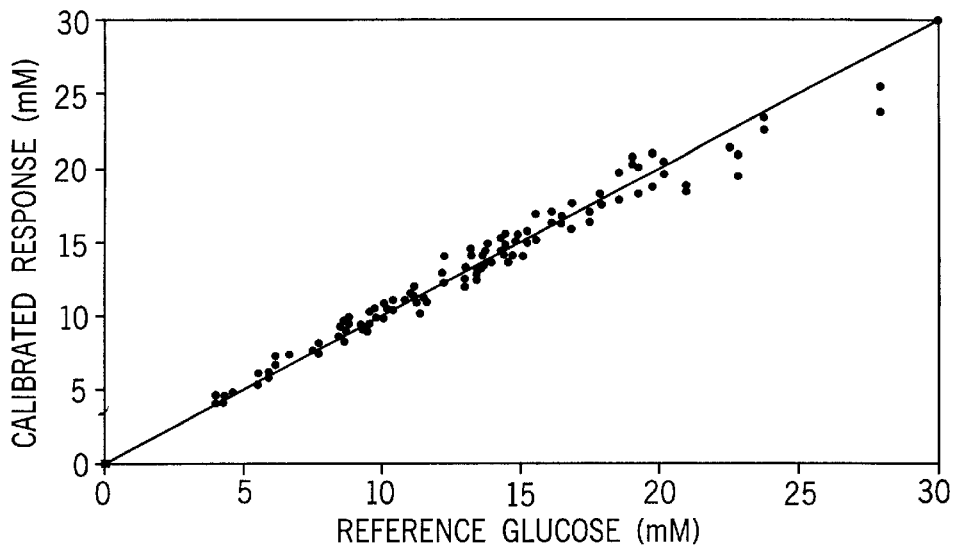
FIG. 3 is a graph summarizing data from tests comparing a conventional electrode strip with an electrode strip having a reduced dead volume. Reference glucose concentration (mM) is on the X axis. Calibrated response (mM) is on the Y axis.

Low volume electrode strips, made as described above, were tested using capillary blood (between 5 and 10 μl) from the fingers of over fifty diabetic patients presenting with a range of blood glucose values between 4 and 27 mM (70 and 500 mg/dl). The calibrated steady state responses given by the electrodes, measured using an appropriate meter (Medisense QID™) were compared against those of a reference whole blood value from a standard laboratory reference analyzer (Yellow Springs, Inc.). The results are plotted in FIG. 3. A linear response from the low volume strips was obtained over this glucose range. Response variability was low, as shown by the small amount of scatter about the linear regression line.

Responses of low volume electrode strips and control strips were compared using blood sample volumes of 10, 5, 4, 3, and 2 μl. Ten replicate samples were applied to each type of electrode strip at each volume. The electrode response, and the number of electrodes giving a measurement response, were measured for each sample volume. The results are summarized in Tables 2 and 3.

TABLE 2

| Sample Volume (μl) | Low Vol. strip Response (μC) | Control Strip Response (μC) |
|---|---|---|
| 10 | 12.5 | 18.2 |
| 5 | 12.3 | 12.4 |
| 4 | 13.4 | 13.1 |
| 3 | 11.9 | 10.2 |
| 2 | 11.7 | |

TABLE 3

Number of Strips Giving a Measurement Response

| Sample Volume (μl) | Low Vol. Strip | Control Strip |
|---|---|---|
| 10 | 10/10 | 10/10 |
| 5 | 10/10 | 10/10 |
| 4 | 10/10 | 8/10 |
| 3 | 10/10 | 3/10 |
| 2 | 7/10 | 0/10 |

The low volume electrode strips continued to give a response even at 2.0 μl, whereas the control strips did not. This demonstrated that the reduced dead volume of the electrode strips of this invention allowed more of the sample to travel to the electrode area and cover the working and reference electrodes. Samples that were too small to completely cover the working electrode area did give a response.

Other embodiments are within the following claims.

We claim:

1. In an elongated electrode strip for performing an electrochemical measurement of glucose in whole blood, in which the electrodes used to perform the measurement are covered with a mesh layer that extends a distance beyond the electrodes along the length of the strip, and the mesh is covered by a liquid impervious layer in which there is an aperture that does not overlay the electrodes, the improvement comprising: a partial occlusion of the mesh that underlays the aperture, which partial occlusion reduces the total volume of blood needed to perform the measurement.

2. In the elongate electrode strip of claim 1, the further improvement comprising occluding at least about 50% of the mesh area underlaying the aperture.

3. The electrode strip of claim 2, wherein a whole blood sample of 2.5 microliters provides sufficient volume of sample to reach the electrodes and cause a measurement.

4. An electrode strip for use in an electrochemical sensor for measuring an analyte in an aqueous sample, comprising:
   an electrode support
   an electrode arrangement on said support, comprising a working electrode and a reference electrode, wherein said working electrode has an upstream end and a downstream end, and said reference electrode is adjacent to said downstream end of said working electrode;
   a hydrophilic mesh layer overlaying a sample loading area and said electrode arrangement, said sample loading area being adjacent to said upstream end of said working electrode;

a cover layer defining an upper boundary of a cell volume encompassing said electrode arrangement;

an aperture in said cover layer, said aperture located above and defining the boundaries of said sample loading area, with no portion of said aperture located above said electrode arrangement;

a dielectric coating impregnated into peripheral regions of said mesh layer, thereby forming an occluded region of said mesh layer, said occluded region overlaying a portion of said sample loading area which lies beneath said aperture and defining side boundaries of said cell volume, said occluded region overlaying no portion of said electrode arrangement;

wherein said mesh layer draws said aqueous sample from said sample loading area onto said electrode arrangement, wherein said aqueous sample contacts said working electrode and said reference electrode.

5. The electrode strip of claim 4, wherein said electrode arrangement further comprises a dummy electrode.

6. The electrode strip of claim 4, comprising one mesh layer.

7. The electrode strip of claim 4, comprising two or more mesh layers.

8. The electrode strip of claim 4, wherein the total thickness of said mesh layer is between 40 and 200 $\mu$m.

9. The electrode strip of claim 4, wherein said mesh layer comprise an inherently hydrophilic mesh material.

10. The electrode strip of claim 4, wherein said hydrophilic mesh layer comprise a mesh material coated with a surfactant.

11. The electrode strip of claim 10, wherein said surfactant is FC 170C FLUORAD™.

12. The electrode strip of claim 11, wherein said mesh material is woven nylon.

13. The electrode strip of claim 4, wherein said mesh layer comprise a woven mesh material having an open area of about 40 to about 45%, a mesh count of about 95 to about 115 strands per centimeter, a strand diameter of about 20 to about 40 $\mu$m, and a thickness of from about 40 to about 60 $\mu$m.

14. The electrode strip of claim 4, wherein said cover layer is substantially impermeable to aqueous liquids.

15. The electrode strip of claim 14, wherein said cover layer consists essentially of a polyester membrane.

16. The electrode strip of claim 4, wherein said electrode strip is between 4.5 and 6.5 mm wide.

17. The electrode strip of claim 16, wherein said aperture has a width between 2.5 and 3.5 mm and a length between 2.5 and 3.5 mm.

18. The electrode strip of claim 4, wherein said dielectric coating is hydrophobic.

19. The electrode strip of claim 4, wherein said occluded region forms a V-shaped sample flow channel in the sample loading area, wherein said V-shaped flow channel widens in the direction of said electrode arrangement.

20. The electrode strip of claim 19, wherein said V-shaped sample flow channel represents between 10 and 50% of the mesh layer area within said aperture.

21. The electrode strip of claim 4, wherein said dielectric coating has a color that contrasts with the color of said cover layer.

22. The electrode strip of claim 4, wherein said dielectric coating has a color that contrasts with the color of said cover electrode support.

* * * * *